United States Patent [19]

Müller et al.

[11] 3,962,041

[45] June 8, 1976

[54] METHOD AND APPARATUS FOR MEASURING THE OPACITY OF FLUIDS

[75] Inventors: Hans Müller, Mannedorf; Werner Stumpp, Stäfa, both of Switzerland

[73] Assignee: Hans Müller, Mannedorf, Switzerland

[22] Filed: Mar. 17, 1975

[21] Appl. No.: 559,156

[30] Foreign Application Priority Data

Mar. 18, 1974 Switzerland.......................... 3809/74

[52] U.S. Cl.................................. 195/127; 356/208
[51] Int. Cl.²........................................... C12K 1/10
[58] Field of Search ............ 195/127, 139; 356/208, 356/180

[56] References Cited

UNITED STATES PATENTS

| | | | |
|---|---|---|---|
| 3,065,148 | 11/1962 | Ferrari................................ | 195/127 |
| 3,531,209 | 9/1970 | Williamson et al................. | 356/180 |

*Primary Examiner*—A. Louis Monacell
*Assistant Examiner*—Robert J. Warden
*Attorney, Agent, or Firm*—Michael J. Striker

[57] ABSTRACT

From a vessel in which micro-organisms grow in a liquid medium containing gas bubbles, a sample is withdrawn into an exterior measuring chamber by means of suction. Gas bubbles are allowed to escape from the sample and thereafter the opacity or turbidity of the sample is measured by passing a light beam through it.

7 Claims, 1 Drawing Figure

U.S. Patent    June 8, 1976    3,962,041
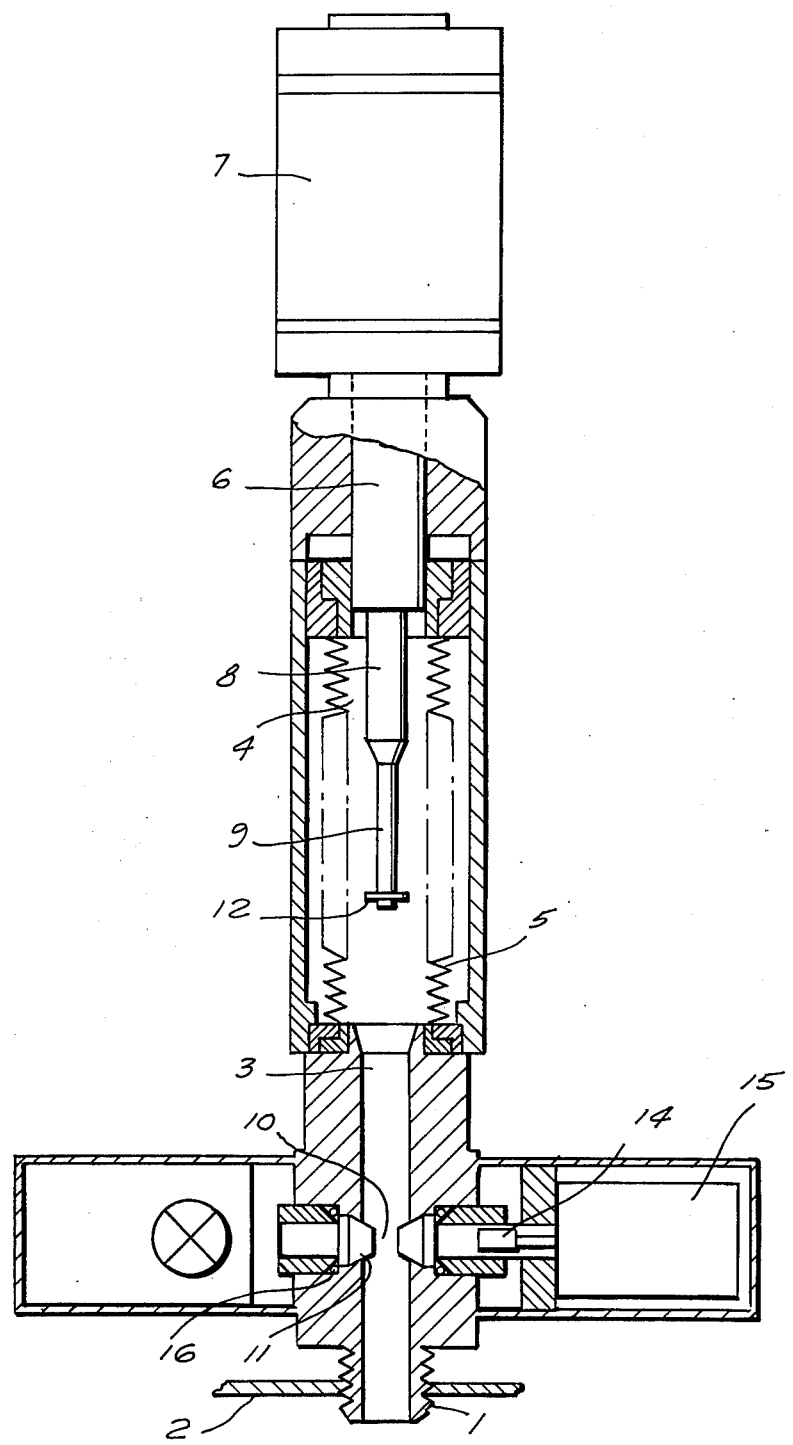

METHOD AND APPARATUS FOR MEASURING THE OPACITY OF FLUIDS

BACKGROUND OF THE INVENTION

The present invention relates generally to the measurement of fluid opacity, and in particular to measuring the turbidity of a fluid in which micro-organisms are growing, for the purpose of monitoring the growth of these organisms.

Still more specifically, the invention relates to a method of carrying out such measurements and to an apparatus for carrying the method into effect.

When micro-organisms are grown in a vessel, for example a so-called "fermentor", their development must be monitored from time to time. This is done by testing the turbidity of the liquid nutrient medium in which they are being grown. The measurements can be taken within the vessel itself or a sample can be removed from the vessel to an exterior measuring chamber. In the latter case it is of course necessary to provide pumps which withdraw the sample and return it subsequently to the vessel, and pumps, the conduits and the separate measuring chamber must be frequently and separately sterilized, i.e. they must be sterilized independently of any sterilization that may be carried out in the vessel at the end of the production of a batch of micro-organisms.

In all prior-art devices the measuring results have not been as accurate as is desirable. The reason for this is that the micro-organisms require for proper growth constant admission of gaseous fluid, such as air or oxygen, into the liquid nutrient medium. This means that the gaseous fluid is present in form of bubbles in the liquid nutrient medium, and when a turbidity measurement is carried out, the presence of these bubbles in the sample of the nutrient medium to be measured tends to adversely affect the accuracy of the measurement. While the problem has been recognized, heretofore no way has been suggested for eliminating gas bubbles from the sample before the measurement is carried out, because the liquid nutrient media and the microorganisms contained therein do not readily lend themselves to a de-gasification prior to carrying out the measurements.

SUMMARY OF THE INVENTION

It is a general object of the present invention to overcome the disadvantages of the prior art.

More particularly it is an object of the present invention to provide an improved method and apparatus for measuring the turbidity of a liquid which contains a gaseous phase.

Another object of the invention is to provide a method and apparatus of this type which permits a photoelectric measurement of the turbidity to be carried out.

An additional object of the invention is to provide such a method and apparatus which does not require outside conduits that present problems in sterilization.

In keeping with these objects and with others which will become apparent hereafter, one feature of the invention resides in a method of measuring the opacity of fluids, particularly of monitoring the growth of microorganisms suspended in a gas-containing liquid medium, by measuring turbidity. The method comprises the steps of drawing a sample of the medium from a vessel into an external measuring chamber, measuring the turbidity of the sample after gas bubbles in the sample have escaped from it, and reintroducing the sample from the measuring chamber into the vessel.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

The single FIGURE illustrates a simplified view of an apparatus for carrying out the present method.

DESCRIPTION OF THE PREFERRED EMBODIMENTS

Reference numeral 2 identifies the wall of a vessel (e.g. a fermentor) which contains liquid nutrient medium wherein micro-organisms are being grown and a gaseous phase, present in form of bubbles in the nutrient medium. The growth of the micro-organisms in this liquid-gas content of the vessel 2 is to be measured, for which purpose the turbidity of the contents is to be determined.

According to the present invention an arrangement is provided which is mounted on the wall 2 by means of screw threads 1 and which has a measuring tube 3, a measuring chamber 4 wherein the de-gasification of the sample is to take place, and a movable bellows 5 (which could be replaced by a diaphragm) that is mounted in the chamber 4. The bellows 5 or the membrane could both be of synthetic plastic material, for instance of polyvinylchloride or the like. A piston rod 6 is provided and is coupled with a drive 7, for instance an electric motor. It is connected with a piston 8 having a lower end portion 9 of reduced diameter. The piston 8 is dimensioned to enter into the opening of the measuring tube 3 and the reduced diameter end portion 9 is dimensioned to enter into an opening 10 at opposite sides of which two lenses of pyrex or quniz glass 11 are provided. The lower end of the end portion 9 carries a wiper plate or round glass 12, e.g., of nylon or the like synthetic plastic that is flexible.

Arranged at the left-hand side of the device is a light source 13 which directs a beam of light across the gap 10 through the two lenses 11, which beam is then received by a photoelectric cell 14 located at the right-hand side, wherein it produces a current whose magnitude depends upon the magnitude of the light beam, and which is amplified at an amplifier 15. A plurality of seals 16, four in the illustrated embodiment, is provided to seal the arrangement with respect to the sample to be measured.

To carry out the method according to the present invention, a sample of the gas-containing liquid nutrient medium is withdrawn from the interior of the vessel 2, by making the piston rod 6 and the piston 8, 9 perform a suction stroke after it has first been moved forwardly (downwardly in the drawing). The resulting expansion of the previously compressed bellows 5, which should preferably be of a heat-resistant synthetic plastic material, causes a sample of the liquid nutrient medium with the micro-organisms and gas bubbles to be drawn via the measuring tube 3 into the degassing chamber 4. In the chamber 4 the sample is allowed to rest for a period of time which is to be determined empirically until the gas bubbles in the liquid have escaped upwardly and left the liquid nutrient medium. The determination of the period of time required for this is very simple and requires no undue experimentation.

After the gas bubbles have so escaped, a light beam is directed across the gap 10 from the light source 14, and when it impinges upon the photoelectric cell 14 it produces a current which is amplified in the amplifier 15 and can then be used to provide the desired information, e.g. to operate a scriber or the like. The magnitude of this current depends upon the intensity of the light beam which travels across the gap 10, and the intensity of the light beam in turn is influenced by the turbidity of the liquid, so that the intensity of the light beam and the magnitude of the current provides an indication of the growth of micro-organisms since these influence the turbidity of the liquid.

After the measurement is complete, the piston 8 is moved downwardly into the measuring tube 3, thereby ejecting the sample back into the vessel 2. During this movement the wiper disc 12 wipes over the lenses 11 and cleans the same. The chamber is now ready for a new measurement to be taken.

When the development of micro-organisms in the contents of the vessel 2 is complete, the contents are removed. Before a new batch of material can be admitted into the vessel, the latter must be sterilized to avoid contamination of the material. This can be carried out in the conventional manner, for example by means of steam, and since there is a direct communication between the vessel and the arrangement according to the present invention, through the gap 10, sterilization of the vessel 2 will at the same time also result in sterilization of the arrangement according to the present invention.

Thus, the disadvantages of the prior art are eliminated, since no complicated equipment is provided which is difficult to sterilize, and since it is now possible to measure the turbidity of the liquid without the presence of the gas bubbles which have deliterious effect on the measurements taken.

It will be understood that each of the elements described above, or two or more together, may also find a useful application in other types of constructions differing from the types described above.

While the invention has been illustrated and described as embodied in a measuring the turbidity of a liquid in which micro-organisms are growing, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Apparatus for measuring the opacity of fluids, particularly for monitoring the growth of microorganisms suspended in a gas-containing liquid medium by measuring turbidity, comprising wall means forming a measuring chamber adapted to be placed into communication with a vessel containing the medium to be measured; suction means for drawing a sample of the medium into the measuring chamber; and measuring means for measuring the turbidity of the sample.

2. Apparatus as defined in claim 1, wherein said measuring means comprises a photoelectric turbidity measuring arrangement.

3. Apparatus as defined in claim 1, wherein said suction means comprises a bellows.

4. Apparatus as defined in claim 1, wherein said suction means comprises a bellows of synthetic plastic material.

5. Apparatus as defined in claim 1, wherein said suction means comprises a synthetic plastic roll membrane.

6. Apparatus as defined in claim 1, wherein said measuring chamber comprises a passage for communication with said vessel; said suction means comprising a piston having a portion adapted to travel in said passage and provided with a wiper for cleaning said passage.

7. Apparatus as defined in claim 6, wherein said measuring means comprises two lenses at opposite sides of said passage; and wherein said wiper is a disc which wipes over said lenses.

* * * * *